United States Patent
Batchelor et al.

(10) Patent No.: US 7,763,283 B2
(45) Date of Patent: *Jul. 27, 2010

(54) NITRIC OXIDE (NO) RELEASING MATERIAL

(75) Inventors: Melissa M. Batchelor, Ann Arbor, MI (US); Bong Kyun Oh, Ann Arbor, MI (US); Mark E. Meyerhoff, Ann Arbor, MI (US)

(73) Assignees: The Regents of The University of Michigan, Ann Arbor, MI (US); Accord Biomaterials, Inc., Ann Arbor, MI (US)

( * ) Notice: Subject to any disclaimer, the term of this patent is extended or adjusted under 35 U.S.C. 154(b) by 801 days.

This patent is subject to a terminal disclaimer.

(21) Appl. No.: 11/523,328

(22) Filed: Sep. 19, 2006

(65) Prior Publication Data

US 2007/0014829 A1   Jan. 18, 2007

Related U.S. Application Data

(63) Continuation of application No. 10/052,239, filed on Jan. 16, 2002, now Pat. No. 7,128,904.

(60) Provisional application No. 60/262,014, filed on Jan. 16, 2001.

(51) Int. Cl.
| A61K 33/34 | (2006.01) |
| A61K 38/44 | (2006.01) |
| A61K 33/00 | (2006.01) |
| A61K 33/26 | (2006.01) |
| A61F 2/00  | (2006.01) |
| C12N 11/00 | (2006.01) |
| C12N 11/02 | (2006.01) |
| C12N 11/08 | (2006.01) |
| C12N 9/04  | (2006.01) |

(52) U.S. Cl. ............. 424/630; 424/94.4; 424/423; 424/426; 424/600; 424/646; 435/174; 435/176; 435/177; 435/180; 435/189

(58) Field of Classification Search .......... None
See application file for complete search history.

(56) References Cited

U.S. PATENT DOCUMENTS

| 3,933,589 A | 1/1976 | Keyes |
| 4,339,448 A | 7/1982 | Dockner et al. |
| 5,169,936 A | 12/1992 | Staples et al. |
| 5,283,339 A | 2/1994 | Arnold et al. |
| 5,294,539 A | 3/1994 | Johannssen et al. |
| 5,386,012 A | 1/1995 | Strid |
| 5,824,673 A | 10/1998 | Abrams et al. |
| 5,834,030 A | 11/1998 | Bolton |
| 5,858,792 A | 1/1999 | Fanning et al. |
| 5,990,289 A | 11/1999 | Fauquex et al. |
| 6,033,368 A | 3/2000 | Gaston, IV et al. |
| 6,143,556 A | 11/2000 | Trachtenberg |
| 6,284,752 B1 | 9/2001 | Abrams et al. |
| 6,569,688 B2 | 5/2003 | Sivan et al. |
| 6,645,518 B2 | 11/2003 | Tedeschi et al. |
| 6,682,732 B1 | 1/2004 | Blake et al. |
| 6,841,166 B1 | 1/2005 | Zhang et al. |
| 7,128,904 B2 * | 10/2006 | Batchelor et al. .......... 424/94.4 |
| 7,335,383 B2 * | 2/2008 | Meyerhoff et al. .......... 424/630 |
| 2002/0115559 A1 | 8/2002 | Batchelor et al. |
| 2004/0224868 A1 | 11/2004 | Meyerhoff et al. |

FOREIGN PATENT DOCUMENTS

| WO | WO 95/04078 | 2/1995 |
| WO | WO 99/09912 | 3/1999 |
| WO | WO 00/02501 | 1/2000 |
| WO | WO 00/11965 | 3/2000 |

(Continued)

OTHER PUBLICATIONS

International Search Report for S.N. PCT/US2006/046013 dated Feb. 20, 2008 (8 pages).

(Continued)

*Primary Examiner*—David M Naff
(74) *Attorney, Agent, or Firm*—Dierker & Associates, P.C.

(57) ABSTRACT

Biocompatible materials that have the ability to release nitric oxide (NO) in situ at the surface-blood interface when in contact with blood. The materials which may be polymers (e.g., polyurethane, poly(vinyl chloride), silicone rubbers), metals, such as stainless steel, carbon, and the like are provided with biocatalysts or biomimetic catalysts on their surface that have nitrite, nitrate, and/or nitrosothiol-reducing capability. Illustratively, the catalysts are adsorbed or immobilized at the surface of the material. The catalysts can act on endogenous nitrite, nitrate, or nitrosothiols within the blood creating a local increase in the NO levels at the surface of the material. An illustrative enzymatic biocatalyst is mammalian xanthine oxidase. In another illustrative embodiment, a biomimetic catalyst is a copper (Cu(II))-ligand complex, e.g. dibenzo[e,k]-2,3,8,9-tetraphenyl-1,4,7,10-tetraaza-cyclododeca-1,3,7,9-tetraene. In some cases, lipophilic salts of nitrite/nitrate (e.g., tridodecylmethylammonium nitrite ($TDMA^+ NO_2^-/NO_3^-$)) or certain salts of nitrosothiols can be doped within a polymer material, or an underlying polymeric film, to create a reservoir of nitrite or nitrosothiol that continuously leaks into the immobilized catalytic layer. Adequate levels of endogenous reducing equivalents are present within blood to provide catalytically-generated surface levels of NO that are above the threshold reportedly required to prevent platelet adhesion or activation.

8 Claims, 4 Drawing Sheets

FOREIGN PATENT DOCUMENTS

| WO | WO 00/12112 | 3/2000 |
|---|---|---|
| WO | WO 00/27887 | 5/2000 |
| WO | WO 02/056904 | 7/2002 |
| WO | WO 2005/011575 | 2/2005 |

OTHER PUBLICATIONS

International Search Report for S.N. PCT/US2004/034613 dated May 18, 2005 (18 pages).
European Search Report for S.N. EP 02 70 75 32 dated Mar. 15, 2005 (5 pages).
Supplemental European Search Report for S.N. EP 02 70 75 32.4 dated Jun. 23, 2005 (8 pages).
Annich, G.M. et al., "Reduced platelet activation and thrombosis in extracorporeal circuits coated with nitric oxide release polymers," Crit. Care. Med. 2000 v. 28 915-920 (6 pages).
Batchelor, M.M. et al., "More Lipophilic Dialkyldiamine-Based Diazeniumdiolates: Synthesis, Characterization, and Application in Preparing Thromboresistant Nitric Oxide Release Polymeric Coatings," J Med Chem (2003), 46: pp. 5153-5161.
Batchelor M.M. et al., "Preparation and characterization of nitric oxide releasing polyurethanes for implantable sensor applications," Sixth World Biomaterials Congress, Kanuela, HI, May 17, 2000, Abstract only (1 page).
Batchelor, M.M. et al., "More biocompatible polyurethanes via nitric oxide release," Abstracts of Papers of the American Chemical Society 222: 405-POLY Part 2, Aug. 2001, Abstract only, (2 pages).
Batchelor, M.M. et al., "More biocompatible polymers via nitric oxide release," University of Washington Engineered Biomaterials Conference, Seattle, WA, Aug. 19, 2001 (1 page).
Batchelor, M.M. et al., "Synthesis of nitric oxide-releasing polyurethane," Proc Am Chem Soc Div PMSE 2001; 84: 594, Abstract only (2 pages).
Batchelor, M.M. et al., "Analytical characterization of novel nitric oxide releasing polymeric films contiaining diazeniumdiolates," Pittsburg Conference New Orleans, LA, Abstract 1217, Mar. 16, 2000, Abstract only (1 page).
Cha, W. et al., "Direct Detection of S-Nitrosothiols Using Planar Amperometric Nitric Oxide Sensor Modified with Polymeric Films Containing Catalytic Copper Species," Anal Chem (2005), 77: pp. 3516-3524.
Cha, W. et al., "S-Nitrosothiol Detection via Ampometric Nitric Oxide Sensor Modified with Polymer film Containing Catalytic Lipophilic Cu(II)-Complex," The Pittsburgh Conference on Analytical Chemistry and Applied Spectroscopy, Orlando, FL (2005), Abstract only, (2 pages).
Chandra, S. et al., "Synthesis and spectral studies on copper (II) complexes of two twelve-membered and tetradentate macrocyclic ligands," Indian Journal of Chemistry, (Dec. 1998), 37A: pp. 1074-1078.
Doel, J. J. et al., "Reduction of Organic Nitrates to Nitric Oxide Catalyzed by Xanthine Oxidase: Possible Role in Metabolism of Nitrovasodilators," Biochemical and Biophysical Research Communications., vol. 270, No. 3, pp. 880-885 (Apr. 2000).
Espadas-Torre, C. et al., "Thromboresistant Chemical Sensors Using Combined Nitric Oxide Release/Ion Sensing Polymeric Films," J Am Chem Soc (1997), 119: pp. 2321-2322.
Fleser, P.S, et al., "Nitric oxide-releasing biopolymers inhibit thrombus formation in a sheep model of arteriovenous bridge grafts," J Vasc Surg 2004, 40: pp. 803-811.
Frost, M.C. et al., "In Vivo biocompatibility and analytical performance of intravascular Clarke-style amperometric oxygen sensors fabricated with NO-releasing polymers," Pittsburgh Conference on Analytical Chemistry and Applied Spectroscopy, Orlando, FL, Mar. 13, 2003, Abstract only (1 page).
Frost, M.C. et al., "Improved in vivo biocompatibility and analytical performance of implanted electrochemical oxygen sensors via nitric oxide release," NAMS, Lexington, KY, May 16, 2001, Abstract only (2 pages).
Frost, M.C. et al., "Improved in vivo biocompatibility and analytical performance of implanted electrochemical oxygen sensors via nitric oxide release," European Society for Biomaterials Meeting, London, England, Sep. 13, 2001, Abstract only (2 pages).
Frost, M.C. et al., "Improved in vivo biocompatibility and analytical performance of implanted electrochemical oxygen sensors via nitric oxide release," Gordon Research Conference on Bioanalytical Sensors, Ventura, CA Mar. 12, 2002, Abstract only (1 page).
Frost, M.C. et al., "Synthesis and characterization of S-nitrosothiol derivatized fumed silica for use as nitric oxide releasing polymer fillers," Society for Biomaterials Meeting, Tampa, FL, Apr. 25, 2002, Abstract only (1 page).
Frost, M.C. et al., Controlled Photoinitiated Release of Nitric Oxide from Polymer Films Containing S-Nitroso-N-acetyl-DL-penicilamine Derivatized Fumed Silica Filler, J Am Chem Soc (2004), 126: pp. 1348-1349.
Frost, M.C. et al., "Improved In Vivo biocompatibility and Analytical Performance of Implanted Electrochemical Oxygen Sensors via Nitric Oxide Release," Society for Biomaterials Meeting, Reno, NV, May 3, 2003, Abstract only (1 page).
Frost, M.C. et al., "Gore-tex vascular grafts with silicone rubbers capable of releasing nitric oxide for sustained times," American Society for Artificial Internal Organs, Washington, DC, Jun. 21, 2003, Abstract only (1 page).
Frost, M.C. et al., "Improved in vivo biocompatibility and analytical performance of implanted electrochemical oxygen sensors via nitric oxide release," Society for Biomaterials Meeting, St. Paul, MN Apr. 27, 2001, Abstract only (1 page).
Frost, M.C. et al., "Synthesis and characterization of S-nitrosothiol derivatized fumed silica used as nitric oxide releasing polymer fillers," American Chemical Society National Meeting, San Diego, CA Apr. 2, 2001, Abstract 345 only (2 pages).
Frost, M.C. et al., "Analytical characterization of S-nitrosothiol derivatized fumed silica," Pittsburgh Conference on Analytical Chemistry and Applied Spectroscopy, New Orleans, LA Mar. 8, 2001, Abstract only (1 page).
Frost, M.C. et al., "Fabrication and In Vivo Evaluation of Nitric Oxide-Releasing Electrochemical Oxygen-Sensing Catheters," Meth Enzymol (2004), 381: pp. 704-715.
Frost, M.C. et al., "Implantable chemical sensors for real-time clinical monitoring: progress and challenges," Curr Opin Chem Biol (2002), 6: pp. 633-641.
Frost, M.C. et al, Polymers incorporating nitric oxide releasing/ generating substances for improved biocompatibility of blood-contacting medical devices, Biomaterials (2005), 26: pp. 1685-1693.
Frost, M.C. et al., "Preparation and characterization of implantable sensors with nitric oxide release coatings," Microchemical Journal, 74 (2003) 277-288.
Frost, M.C. et al., "Synthesis, characterization, and controlled nitric oxide release from S-nitrosothiol-derivatized fumed silica polymer filler particles," J Biomed Mater Res A (2005), 72A: pp. 409-419.
Frost, M.C. et al., "In Vivo Biocompatibility and Analytical Performance of Intravascular Amperometric Oxygen Sensors Prepared with Improved Nitric Oxide Releasing Silicone Rubber Coating," Anal Chem (2002), 74: pp. 5942-5947.
Hwang, S.Y. et al., "Covalently attached Cu(II)-complex hydrogel as novel hemocompatible materials," Abstracts of Papers of the American Chemical Society 228: 292-POLY, Part 2 Aug. 22, 2004, 228th National Meeting of the American-Chemical-Society, Philadelphia, PA, Aug. 22-26, 2004, Abstract only (3 pages).
Hwang, S.Y. et al., "Covalently attached Cu(II)-complex hydrogel as novel hemocompatible materials," Abstracts of Papers of the American Chemical Society 228: 292-Poly, Part 2 Aug. 22, 2004, 228th National Meeting of the American-Chemical-Society, Philadelphia, PA, Aug. 22-26, 2004, Amer Chem Soc.
Lee, Y. et al., "Improved Planar Amperometric Nitric Oxide Sensor Based on Platinized Platinum Anode. 1. Experimental Results and Theory When Applied for Monitoring NO Release from Diazeniumdiolate-Doped Polymer Films." Anal Chem (2004); 76: pp. 536-544.
Lee, Y. et al., "Improved Planar Amperometric Nitric Oxide Sensor Based on Platinized Platinum Anode. 2. Direct Real-Time Measurement of NO Generated from Porcine Kidney Slices in the Presence of L-Arginine, L-Arginine Polymers, and Protamine," Anal Chem (2004), 76: pp. 545-551.

Meyerhoff, M.E., "Use of Nitric oxide Releasing/Generating Polymeric Coatings to Enhance the Biocompatibility of Implanted Chemical Sensors," $229^{th}$ American Chemical Society Meeting, San Diego, CA, Mar. 2005, Analytical 340, Abstract only (1 page).

Meyerhoff, M.E. et al., "Intravascular Chemical Sensors: Can in Situ Nitric Oxide Release Solve Lingering Blood compatibility/Analytical Performance Problems?" The Pittsburgh Conference on Analytical Chemistry and Applied Spectroscopy, New Orleans, LA, Abstract 1188, (2000), Abstract only (1 page).

Meyerhoff, M.E., "Improving the bioanalytical chemistry of in vivo chemical sensors using controlled nitric oxide release," Abstracts of Papers of the American Chemical Society 228: 132-ANYL, Part 1 Aug. 22, 2004, 228th National Meeting of the American-Chemical-Society, Philadelphia, PA, Aug. 22-26, 2004, (1 page).

Meyerhoff, M.E. et al., Enhancing the biocompatibility and in vivo performance of intravascular chemical sensors using nitric oxide release polymers. Abstracts of Papers of the American Chemical Society 218: U165-U165 132-ANYL Part 1, Aug. 22, 1999, Abstracts only (2 page).

Mowery, K.A. et al., "More Biocompatible Electrochemical Sensors Using Nitric Oxide Release Polymers," Electroanalysis (1999), 11: pp. 681-686.

Mowery, K.A. et al., "Preparation and characterization of hydrophobic polymeric films that are thromboresistant via nitric oxide release," Biomaterials (2000), 21: pp. 9-21.

Mowery, K.A, et al., "The transport of nitric oxide through various polymeric matrices," Polymer Commun(1999), 40: pp. 6203-6207.

Mowery, K.A. et al., "Thromboresistant Ion-Selective Electrodes Via Nitric Oxide Release Polymeric Membranes," The Pittsburgh Conference on Analytical Chemistry and Applied Spectroscopy, New Orleans, LA (1998), Abstract only (1 page).

Mowery, K.A. et al., "Polymeric diazeniumdiolates for fabricating thromboresistant electrochemical sensors via nitric oxide release," Abstracts of Papers of the American Chemical Society 216: U821-U821 034-PMSE Part 2, Aug. 23, 1998, Abstract only (2 pages).

Mowery, K.A. et al., "More biocompatible electrochemical sensors through the use of combined nitric oxide release ion sensing polymeric films," Abstracts of Papers of the American Chemical Society 213: 339-PMSE Part 2, Apr. 13, 1997, Abstract only (2 pages).

Mowery, K.A. et al., "More Biocompatible electrochemical sensors using nitric oxide release polymers," International Symposium on Electrochemical and Biosensors, Matrafured, Hungary 1998 (2 pages).

Negele, J.C. et al., "Nitric-oxide releasing indwelling oxygen sensors: Thromboresistivity and performance in dogs," Anesthesia and Analgesia 90 (2): U90-U90 S134 Suppl. S, Feb. 2000, Abstract only (1 page).

Oh, B.K. et al., "Spontaneous Catalytic Generation of Nitric Oxide from S-Nitrosothiols at the Surface of Polymeric Films Doped with Lipophilic Copper(II) Complex," J Am Chem Soc (2003), 25: pp. 9552-9553.

Oh, B.K. et al., "Direct Electrochemical Measurement of Nitric Oxide Release Profile from Diazeniumdiolate Doped Polymer Films," Presentation 340, Pittsburg Conference New Orleans, LA, 2000, Abstract only (1 page).

Oh, B.K. et al., "Study of Ion Mediated Reduction of Nitrite to Nitric Oxide (NO) by Ascorbate," Presentation 646, Pittsburg Conference New Orleans, LA, 2001, Abstract only (1 page).

Oh, B.K. et al., "Copper-Complex Mediated Nitrite Reduction to Nitric Oxide (NO) at the Polymer/Solution Interface by L-Ascorbate," Society for Biomaterials Meeting—$28^{th}$ Annual, Tampa, FL, Apr. 25, 2005, Abstract only (1 page).

Oh, B.K. et al., "Catalytic generation of nitric oxide from nitrite at the interface of polymeric films doped with lipophilic Cu(II) complex: a potential route to the preparation of thromboresistant coatings," Biomaterials (2004), 25: pp. 283-293.

Oh, B. K. et al., Biomimetic nitric oxide (NO) generation at interface of polymeric materials doped with lipophilic copper(II)-complex,: Dissertation Abstracts International, vol. 64, No. 9B, p. 4325 (one page) (2003).

Parzuchowski, P.G. et al., "Synthesis and Characterization of Polymethacrylate-Based Nitric Oxide Donors," Am Chem Soc (2002), 124: pp. 12182-12191.

Parzuchowski, P.G. et al., "Synthesis of potentially more blood compatible nitric oxide releasing acrylic copolymers," Abstracts of Papers of the American Chemical Society 221: U298-U298 27-POLY Part 2, Apr. 1, 2001, Abstract only (2 pages).

Reynolds, M.M. et al., "Nitric Oxide Releasing Hydrophobic Polymers: Preparation, Characterization, and Potential Biomedical Applications," Free Rad Biol Med (2004), 37: pp. 926-936.

Reynolds, M.M., "Biomimetic Surfaces for Vascular Devices," $8^{th}$ UWEB Summer Symposium, Poster Presentation, Seattle, WA, Aug. 25, 2004, Abstract only (1 page).

Roy-Chaudhury, P. et al., "Local nitric oxide delivery systems: Implications for transplant preservation," American Journal of Transplantation 4: 842, Suppl. 8 2004, American Transplant Congress, Boston, MA, May 14-19, 2004, Amer Soc Transplant Surg; Amer Soc Transplant, Abstract only (1 page).

Roy-Chaudhury P. et al., "Local nitric oxide delivery systems for dialysis access grafts," Journal of the American Society of Nephrology 14: 508A-508A, Suppl. S Nov. 2003, 36th Annual Meeting of the American-Society-of-Nephrology, San Diego, California, Nov. 12-17, 2003, Amer Soc Nephrol SA-PO950, Abstract only (1 page).

Saavedra, J.E. et al., "Conversion of a Polysaccharide to Nitric Oxide-Releasing Form. Dual-Mechanism Anticoagulant Activity of Diazeniumdiolated Heparin," Bioorg Med Chem Letters (2000), 10: pp. 751-753.

Schoenfisch et al., "Improving the Thromboresistivity of Chemical Sensors via Nitric Oxide Release: Fabrication and in Vivo Evaluation of NO-Releasing Oxygen-Sensing Catheters," Anal. Chem. (2000) 72: pp. 1119-1126.

Schoenfisch, M.H. et al., "Nitric Oxide Releasing Fluorescence-Based Oxygen Sensing Polymeric Films," Anal Chem (2002), 74: pp. 5937-5941.

Schoenfisch, M.H. et al., "Improving the biocompatibility of intravascular amperometric oxygen sensors via nitric oxide release," Abstracts of Papers of the American Chemical Society 216: U158-U158 062-ANYL Part 1, Aug. 23, 1998, Abstract only (2 pages).

Schoenfisch, M.H. et al. "Thromboresistant Fluorescent Optical Sensors via Nitric Oxide Release," The Pittsburgh Conference on Analytical Chemistry and Applied Spectroscopy, Abstract 728, (1999), Abstract only (1 page).

Wu, Y., "In Situ Generation of Nitric Oxide (NO) at Polymer/Blood Interface: Enhancing the Thromboresistivity of Intravascular chemical Sensors and Other Biomedical Devices," Poster presentation. $8^{th}$ UWEB Summer Symposium, Seattle, WA, Aug. 25, 2004, Abstract only (1 page).

Ye, Q. et al., "Surface Morphology of Thrombsoresistant Nitric Oxide Release Polymeric Membranes," The Pittsburgh Conference on Analytical Chemistry and Applied Spectroscopy, New Orleans, LA, Abstract 334, (2000), Abstract only (1 page).

Zhang, H. et al., "Nitric oxide releasing silicone rubbers with improved blood compatibility: preparation, characterization, and in vivo evaluations," Biomaterials (2002), 23: pp. 1485-1494.

Zhang, H. et al., "Polymer Films or Coatings Embedded with Nitric Oxide Releasing Fumed Silica Particles," The $222^{nd}$ American Chemical Society National Meeting, Chicago, IL, United States, Aug. 26-30, 2001, Abstract only (2 pages).

Zhang, H. et al., "Novel Silicone Materials with Improved Thromboresistance via Nitric Oxide Release," The $221^{st}$ American Chemical Society National Meeting, San Diego, CA, United States, Apr. 1-5, 2001, Abstract only (2 pages).

Zhang, H. et al., "Potentially More Blood Compatible Polymers Using Nitric Oxide Release Fumed Silica as Fillers," The $220^{th}$ American Chemical Society National Meeting, Washington DC, United States, Aug. 20-24, 2000, Abstract only (3 pages).

Zhang, H. et al., "More Blood Compatible Silicone Rubbers via Nitric Oxide Release," The $6^{th}$ World Biomaterials Congress, Hawaii, United States, May 15-20, 2000, Abstract only (2 pages).

Zhang, H. et al., "Synthesis of Nitric Oxide Releasing Silicone Rubbers for Biomedical Applications," The $218^{th}$ American Chemical Society National Meeting, New Orleans, LA, United States, Aug. 22-26, 1999, with Abstract (4 pages).

Zhang, H. et al., "Nitric Oxide-Releasing Fumed Silica Particles: Synthesis, Characterization, and Biomedical Application," J Am Chem Soc (2003), 125: pp. 5015-5024.

Zhou, Z. et al., "Combining Nitric Oxide Release with Surface Bound Heparin: A Potentially More Thromboresistant Polymeric Coating for Medical Devices," The University of Washington Engineered Biomaterials 8$^{th}$ Summer Symposium, University of Washington, Seattle, WA, USA, Aug. 25-27, 2004, Abstract only (1 page).

Zhou Z.R. et al., "Design, synthesis and characterization of nitric oxide releasing acrylic copolymers with potentially improved blood compatibility," Abstracts of Papers of the American Chemical Society 226: 542-POLY, Part 2 Sep. 2003, 226th National Meeting of the American-Chemical-Society, New York, New York, Sep. 7-11, 2003, Amer Chem Soc 19, Abstract only (2 pages).

* cited by examiner

SCHEMATIC OF SURFACE NO GENERATION VIA
NITRITE REDUCTASE ACTIVITY AND
POLYMER LOADED WITH NITRITE SALT

R= TRIDODECYLMETHYLAMMONIUM

NO RELEASING PROFILE FROM NITRITE ION-PAIR
DOPED POLYMER FILMS IN SHEEP BLOOD

*DISTANCE BETWEEN POLYMER SURFACE
AND SENSOR IS 10 $\mu m$

ASC: ASCORBATE, DA: DEHYDROASCORBATE, X⁻: ANION $Cu^{2+}$ : LIPOPHILIC COPPER COMPLEX $Cu^{2+}$ : Cu(II) COMPLEX
ASC: ASCORBATE
DA: DEHYDROASCORBATE
RSNO: NITROSOTHIOL

NITRIC OXIDE (NO) RELEASING MATERIAL

CROSS REFERENCE TO RELATED APPLICATIONS

This application is a continuation of U.S. patent application Ser. No. 10/052,239, filed on Jan. 16, 2002 now U.S. Pat. No. 7,128,904, which claims the benefit of U.S. Provisional Patent Application Ser. No. 60/262,014 filed on Jan. 16, 2001.

STATEMENT REGARDING FEDERALLY SPONSORED RESEARCH OR DEVELOPMENT

This invention was made in the course of research partially supported by a grant from the National Institutes of Health, Grant Number GM 56991. The U.S. government has certain rights in the invention.

BACKGROUND

This invention relates generally to biocompatible materials, such as polymers or metals, and more particularly, to biocompatible materials having blood interface surfaces that are capable of biocatalytic or biomimetic generation of nitric oxide in situ when contacted with endogenous nitrite, nitrate, or nitrosothiols in blood.

Although medical devices such as extracorporeal circuits and hemodialysis tubes are widely used in clinical settings, the polymers typically used to fabricate such devices (PVC, polyurethane, silicone rubber, etc.) are still subject to platelet aggregation and adhesion onto the surface of these materials. Thus, patients are often given anti-clotting agents (i.e., heparin) in order to reduce thrombosis on the surface of these devices. Similarly, implanted devices made of stainless steel or other alloys, or even carbon, can cause thrombus formation when in direct contact with blood. There is, therefore, a need for materials that more closely simulate the antithrombogenic properties of the endothelial cells that line blood vessels in order to obviate the need to administer anticoagulants.

Nitric oxide (NO) is an important intracellular and intercellular messenger molecule that plays an important physiological role in anti-platelet aggregation and anti-platelet activation, vascular relaxation, neurotransmission, and immune response. It has been proposed that synthetic materials that release low levels of NO would, therefore, more closely simulate the natural activity of endothelial cells, and therefore, would have improved biocompatibility.

Several classes of NO-releasing materials are currently under investigation worldwide. These include NO donors (i.e., diazeniumdiolates, nitrosothiols) that may be relatively complicated to synthesize and may, in some instances, require stringent storage conditions. Thus, there is a need for improved materials that are easier to fabricate and store.

Currently, NO generation is determined by water uptake (such as in the case of diazeniumdiolates) or the intensity of light (as with iron nitrosyls). However, blood already contains a host of species that are derived from, or are physiologically-generated in vivo that can be reduced to NO. These species include nitrites, nitrates, and a host of nitrosothiols (e.g., nitrosoglutathione, nitroso albumin, etc.). This raises the possibility of recycling these species back to nitric oxide. There is, therefore, a need for materials that can reduce these species to nitric oxide locally at the substrate/blood interface.

It is an object of this invention to provide improved materials for biomedical applications that are capable of releasing NO from blood-contacting surfaces materials, so as to prevent platelet activation and adhesion onto these surfaces, thereby lowering thrombus formation and other complications associated with interactions between blood and foreign materials.

It is a further object of this invention to provide improved materials for biomedical applications that are relatively inexpensive to manufacture and that have improved biocompatibility.

It is still a further object of this invention to provide materials for biomedical applications that are capable of releasing NO from blood-contacting surfaces materials in response to nitrites, nitrates, and nitrosothiols in the blood.

SUMMARY

The foregoing and other objects are achieved by embodiment(s) of this invention, which provide a novel approach for enhancing the biocompatibility of materials of the type suitable for implantation in a human or animal body and/or for prolonged contact with the body or blood. In accordance with a broad aspect of the invention, materials have been developed to have a catalytic surface that is capable of generating, at the catalytic surface/blood interface, physiologically significant amounts of NO when in contact with blood. A catalytic agent, having nitrite reductase activity and/or nitrite reductase-like activity, or nitrosothiol reductase activity, is immobilized, adsorbed, adhered, or otherwise made available at a surface of the material.

In some embodiments, the catalytic agents are biocatalysts, such as enzymes, having nitrite reductase and/or nitrite reductase-like activity, or nitrosothiol reductase activity. Illustrative examples of the biocatalyst include nitrite reductases, nitrate reductases, enzymes having nitrosothiol reducing ability, and xanthine oxidase, or combinations thereof. Due to the ease of procuring xanthine oxidase commercially (e.g., Sigma, St. Louis, Mo.), xanthine oxidase is a preferred embodiment. Other potentially useful immobilized biocatalysts include nitrite reductases and nitrate reductases from plants or bacteria.

In other embodiments, the catalytic agent is a biomimetic catalytic agent. As used herein the term "biomimetic catalytic agent" refers to a species possessing nitrite reductase-like activity, or the ability to reduce nitrosothiols which converts endogenous or exogenous nitrite/nitrate or nitrosothiols to NO when in contact with blood.

Illustratively, the biomimetic catalytic agent is a metal ion ligand complex wherein the metal ion is capable of reducing one or more of nitrite, nitrate, nitrosothiols, and other blood species to nitric oxide. In particularly preferred embodiments, the metal ion ligand complex is a Cu(II) complex. Neutral carrier type ligands that have high metal binding affinity, particularly for copper, are suitable for use in the practice of the invention. Further suitable neutral carrier type ligands include those having planar square-type geometry that provides a minimum amount of steric hindrance to the approach of the electron source (e.g., ascorbate or NADH) to the center metal of the complex so that the copper ion can easily be reduced from Cu(II) to Cu(I). Examples include, without limitation, nitrogen or sulfur donating compounds, such as $N_x$-donor s (x=2, 4, 5, 6, 8) such as cyclen, cyclam and their derivatives, and crown ethers and $S_x$-donor macrocyle-type ligands (x=2, 4, 5, 6, 8).

In specific illustrative embodiments, the biomimetic catalyst is a Cu(II) metal ion ligand complex selected from the group consisting of dibenzo[e,k]-2,3,8,9-tetraphenyl-1,4,7,10-tetraaza-cyclododeca-1,3,7,9-tetraene; dibenzo[e,k]-2,3,8,9-tetramethyl-1,4,7,10-tetraaza-cyclododeca-1,3,7,9-tetraene; and dibenzo[e,k]-2,3,8,9-tetraethyl-1,4,7,10-tetraaza-cyclododeca-1,3,7,9,-tetraene.

As used herein, the term "material," when referring to the material that is provided with the catalytic surface, may be any material. In an embodiment, the material is of a type that is suitable for contact with the body and/or body fluids, particularly blood, of a living being, e.g., a material that is physiologically acceptable and non-toxic. In some embodiments, the material should be suitable for long-term contact, or indwelling uses. Non-limitative examples of such materials include polymers, metals and alloys thereof, and carbon (graphite).

Many polymeric materials are suitable for the practice of the invention, and the following illustrative list of polymers that has been used for biomedical applications, is not intended to be limiting in any manner. Examples include synthetic polymers such as polyurethane, polydimethylsiloxane, ethylene vinyl acetate, nylons, polyacrylic, polymethyl methacrylate, polyamide, polycarbonate, polyester, polyethylene, polypropylene, polystyrene, poly(vinyl chloride) (PVC), polytetrafluoroethylene (PTFE), and cellulose acetate.

In an embodiment, the material includes a hydrophobic polymer substrate, such as poly(vinyl chloride), polyurethane, and silicone rubber, and a layer of a catalytic agent having nitrite reductase activity and/or nitrite reductase-like activity, or nitrosothiol reductase activity attached to a surface of the hydrophobic polymer substrate. The attachment may be by adsorption, covalent bonding, and the like. In an embodiment, the polymer substrate may include lipophilic salts of nitrite, nitrates, or nitrosothiols within its matrix to create a reservoir of nitrite, nitrate, or nitrosothiol that can continuously leak to the catalytic surface.

In embodiments where the "material" is a polymer, the NO-releasing polymer can be formed, cast, or otherwise shaped to form a monolithic device, such as an implantable device (e.g. a drug depot) or in-dwelling devices, (e.g. catheters, or extracorporeal tubing sets (non-limitative examples include kidney dialysis or open-heart surgery heart-lung machines)) and/or the like. The polymer may also be applied as a film on another substrate, such as, for example, a polymer substrate, or on another surface, such as, for example, the surface of a metal device.

Suitable metals include, but are not limited to, stainless steel, nickel, titanium, aluminum, copper, gold, silver, platinum and combinations thereof. The metal material may form medical devices. The following types of devices, provided with a catalytic agent in accordance with the principles of the invention, are meant to be illustrative, but not limiting, examples: arterial stents, guide wires, catheters, bone anchors and screws, protective platings, hip and joint implants, spine appliances, electrical leads, biosensors, and probes.

Further, the material may be a metal substrate. In an embodiment, the metal substrate may have a biomimetic catalytic agent covalently attached to its surface. As stated above, in an embodiment, the biomimetic catalytic agent is a metal ion ligand complex which is capable of reducing one or more of nitrite, nitrate, nitrosothiols, and other blood species to nitric oxide. In particularly preferred embodiments, the biomimetic catalytic agent is a Cu(II) metal ion ligand complex. Attachment of the metal ion ligand to the metal surface may be accomplished by any suitable means. One such technique involves silanizing the surface of the metal to provide reactive sites to bind the ligand.

In certain embodiments, an exogenous source of nitrites, nitrates, or nitrosothiols is provided in the polymer to form a reservoir of nitrite, nitrate, or nitrosothiol that can continuously leak to the catalytic surface of the material. In these embodiments, the exogenous source (a non-limitative example of which includes lipophilic salts of nitrites, nitrates, or nitrosothiols) is dispersed within the material. In some embodiments, the polymeric material containing the exogenous source of nitrite/nitrate or nitrosothiol is applied to a catalytic surface as a coating. Some non-limitative examples of the source of nitrites, nitrates, or nitrosothiols, include, without limitation, quaternary ammonium salts, such as tridodecylmethylammonium nitrite (TDMA$^+$ NO$_2^-$/NO$_3^-$); trimethyl phenyl ammonium; dimethyl dioctadecyl ammonium; etc. In addition to quaternary ammonium salts, quaternary phosphonium salts or quaternary arsonium salts may be used in the practice of embodiments of the invention.

Methods of making the invention include swelling a polymer, such as a poly(vinyl chloride) (PVC) or silicone, in the presence of an organic solvent containing an appropriate nitrite/nitrate salt to form a nitrite/nitrate salt-containing polymer. The nitrite/nitrate salt-containing polymer is then coated with a layer of immobilized enzyme, illustratively a nitrite reductase enzyme, such as xanthine oxidase. Many techniques are available for immobilizing enzymes. For example, see, Hasselberger, "Uses of Enzymes and Immobilized Enzymes, Nellson-Hall," Chicago (1978) or Guilbault, "Analytical Uses of Immobilized Enzymes," Marcel Dekker, New York (1984).

In another embodiment of the method, the biomimetic generation of NO may be achieved by immobilizing metal-ion ligand complexes, on the surface of the material, or by dispersing these ligands within the material, which may be a polymer. In some embodiments, additional lipophilic nitrite/nitrate salts, or nitrosothiols, are added to an underlying polymer matrix material or provided as a coating on the material, or as an additional layer.

BRIEF DESCRIPTION OF THE DRAWINGS

Comprehension of embodiment(s) of the invention is facilitated by reading the following detailed description, in conjunction with the annexed drawing, in which.

DETAILED DESCRIPTION

In one embodiment of the method for making an improved NO-releasing polymer, the desired polymer may be swelled in an organic solution containing the lipophilic nitrite/nitrate salt. In other embodiments, the salt can be added during the processing stage when the desired end product is molded or cast from the native polymer material. In still other embodiments, the surface of the polymer material that will be exposed to blood (non-limitative examples of which include the outside surface of a catheter, the inner surface of tubing of the type used in extracorporeal circuits, or the surface of metal stents) may be coated, either by dip-coating or by another method, with a biocatalyst (enzyme) or biomimetic catalyst capable of reducing nitrate, nitrite, or nitrosothiols to NO. The biocatalysts or biomimetic catalysts can also be covalently tethered to the surface of the material.

Figure 1:
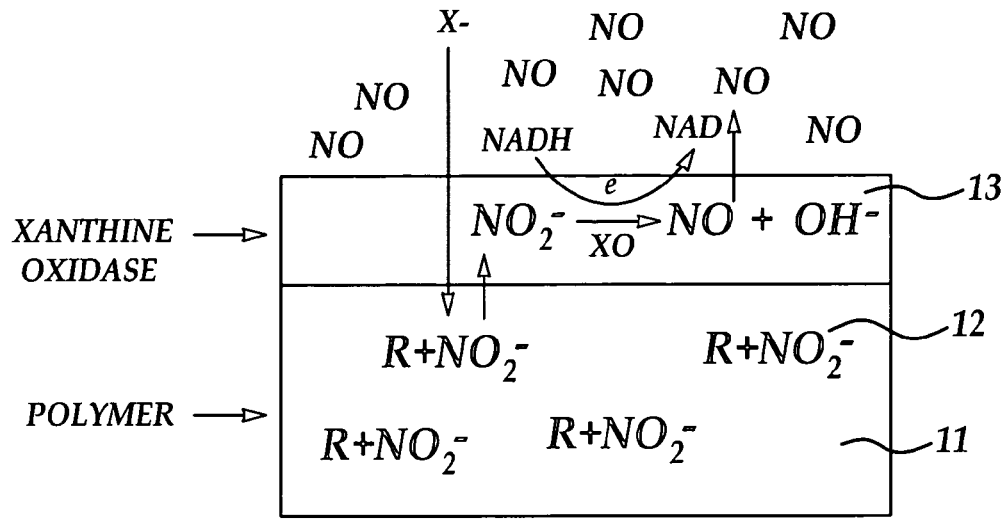
FIG. 1 is a schematic illustration of NO generation in solution via nitrite reductase activity from the catalytic surface of a polymer loaded with nitrite salt.

FIG. 1 illustrates a specific embodiment of the material of the present invention. Mammalian xanthine oxidase (XO) is used as the surface catalyst for nitrite reduction to NO. In the presence of nicotinamide adenine dinucleotide (NADH), or other reducing equivalents in blood, the surface catalyst will generate NO as the nitrite ions leak from within the material into this surface layer via exchange for chloride and bicarbonate within the blood. Referring to FIG. 1, a polymer matrix 11 that has been loaded with a lipophilic nitrite/nitrate salt of tridodecylmethylammonium 12 ($R^+NO_2^-$) that provides a source of nitrite ions ($NO_2^-$). A coating 13 of xanthine oxidase (XO) is located at the surface of the polymer matrix 11.

Preliminary feasibility studies have been carried out to demonstrate the basic concept of this invention. Xanthine oxidase was used as a model enzyme for nitrite reductase activity. PVC polymer films were doped with $TDMA^+ NO_2^-$ and then coated with a layer of immobilized XO.

Illustratively, the PVC polymeric film, or membrane, was prepared by a cocktail solution casting method as described, for example, in Mathison et al., Anal. Chem., Vol. 71, pages 4614-4621 (1999) or any of the patents referenced herein. The cocktail solution was prepared by dissolving the appropriate amounts of membrane components (polymer, plasticizers and, in some cases, an ion-exchanger) into a solvent, illustratively tetrahydrofuran (THF). The membranes were cast in a mold to a final thickness of about 150 μm.

The polymer film was then coated with immobilized XO, prepared by crosslinking XO with bovine serum albumin (BSA) in the presence of glutaraldehyde. The cross-linked product forms a hydrogel that is dip-coated on the PVC polymer substrate.

An electrochemical sensor was used to probe the surface concentrations of NO generated when the coated film was placed into a buffered solution containing NADH at physiological pH. Significant levels of NO were generated at the surface of the film under these conditions. The generation of NO near the surface of the polymer film continued for several hours as the nitrite in the film was exchanged for anions in the buffer phase.

In this particular embodiment, the electrochemical NO sensor used was similar in style to a conventional Clark type oxygen sensor. A glass coated Platinum (Pt) wire served as the anode and a Ag/AgCl wire (0.25 mm dia.) was used as the cathode. The internal filling solution was composed of 0.3 mM HCl and 30 mM NaCl, pH 3.5. An outer gas permeable membrane (Goretex, polytetrafluoroethylene with 50% porosity and 0.2 μm pore size) was placed between the internal filling solution and sample solution. Amperometric NO measurements were performed using an electrochemical analyzer.

Figure 2:
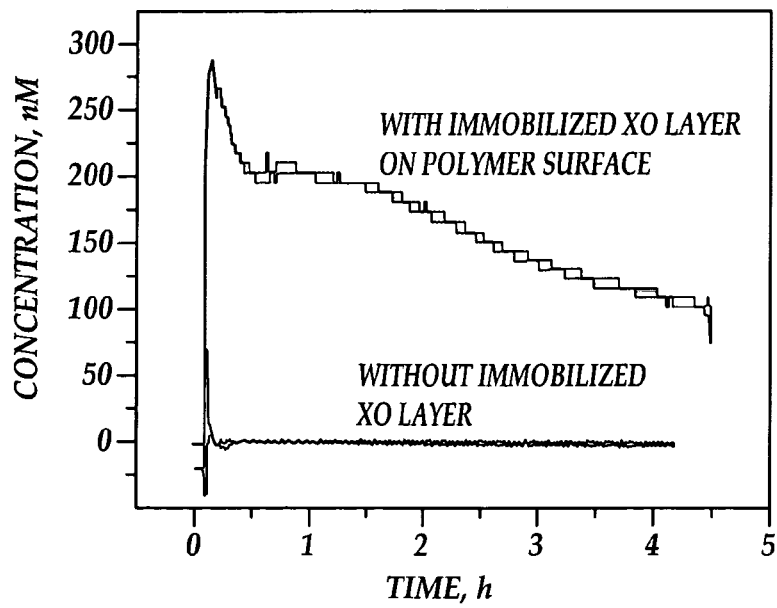
FIG. 2 is a graphical representation of the NO-release profile from nitrite ion-pair doped polymer films having immobilized XO on the surface in the presence of sheep blood.

FIG. 2 graphically illustrates that, when a similar film coated with XO was exposed to whole sheep blood, without the addition of any reducing equivalents in the form of NADH, measurable levels of NO were generated at the surface of the film as detected by the aforementioned electrochemical NO sensor. This data suggests that there is adequate endogenous reducing equivalent species in blood to serve as the source of electrons for the biocatalytic reaction at the surface of a polymer prepared in accordance with the present invention.

In another illustrative embodiment, biomimetic catalysts, such as Cu(II)-ligand complexes, for example, dibenzo[e,k]-2,3,8,9-tetraphenyl-1,4,7,10-tetraaza-cyclododeca-1,3,7,9-tetraene, were either incorporated in or tethered to a polymer or other material surface, such as a metal. Examples of this embodiment are shown in FIGS. 3 and 4.

Figure 3:
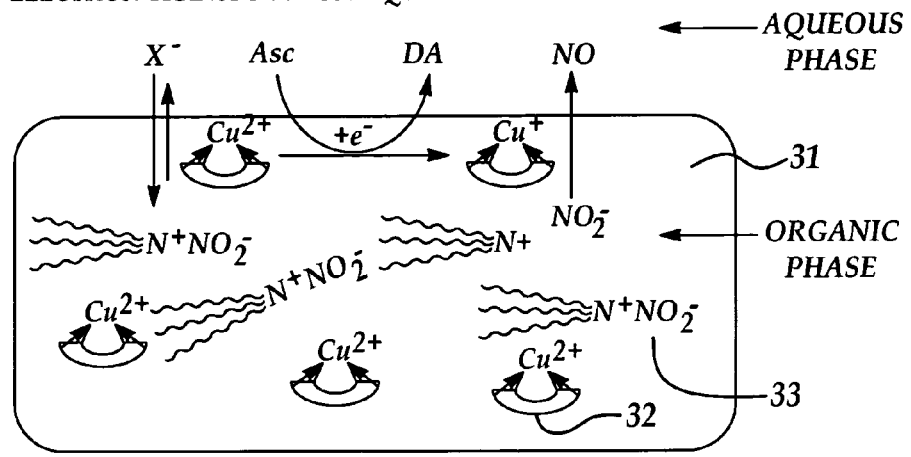
FIG. 3 is a schematic representation of NO generation from a polymer matrix that has been loaded with a nitrate salt and a Cu(II) ligand complex in accordance with the invention.

FIG. 3 is a schematic representation of a polymer matrix 31, illustratively PVC, that has been loaded with a lipophilic Cu(II) ligand complex 32 as well as a lipophilic nitrite/nitrate salt of tridodecylmethylammonium 33 ($N^+NO_2^-$) that provides a source of nitrite ions ($NO_2^-$) in the polymer. When the polymer 31 is exposed to an aqueous solution containing ascorbate (ASC) or ascorbic acid, the ascorbic acid reduces the Cu(II) in the ligand complex 32 to Cu(I). The Cu(I) in turn reduces nitrites in the film to NO.

Figure 4:
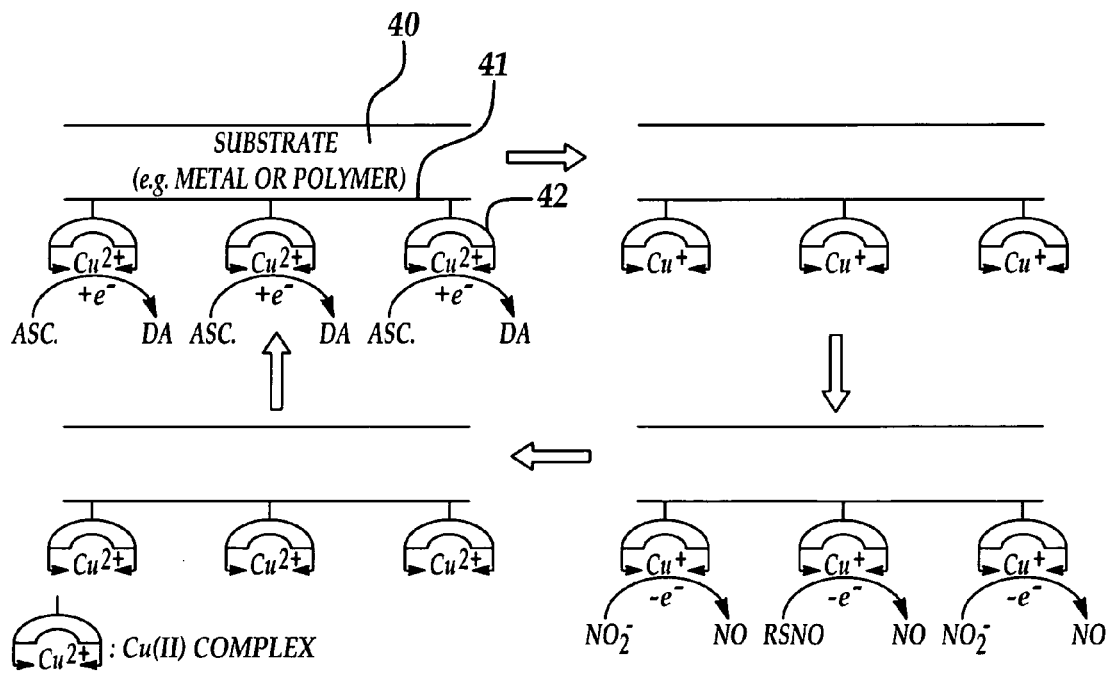
FIG. 4 is a schematic representation of a material, in accordance with the invention, wherein a Cu(II) ligand complex is covalently tethered to the surface.

FIG. 4 is a schematic representation of a material 40 that has a catalytic surface 41 created by tethering a Cu(II) ligand complex 42 to the surface. When the catalytic surface 41 is exposed to an aqueous solution, which may be blood, containing ascorbic acid, the ascorbic acid reduces Cu(II) in the ligand 42 to Cu(I). The Cu(I) returns to Cu(II), thereby converting nitrites and nitrosothiol (RSNO), for example, in the solution to NO.

Figure 5:
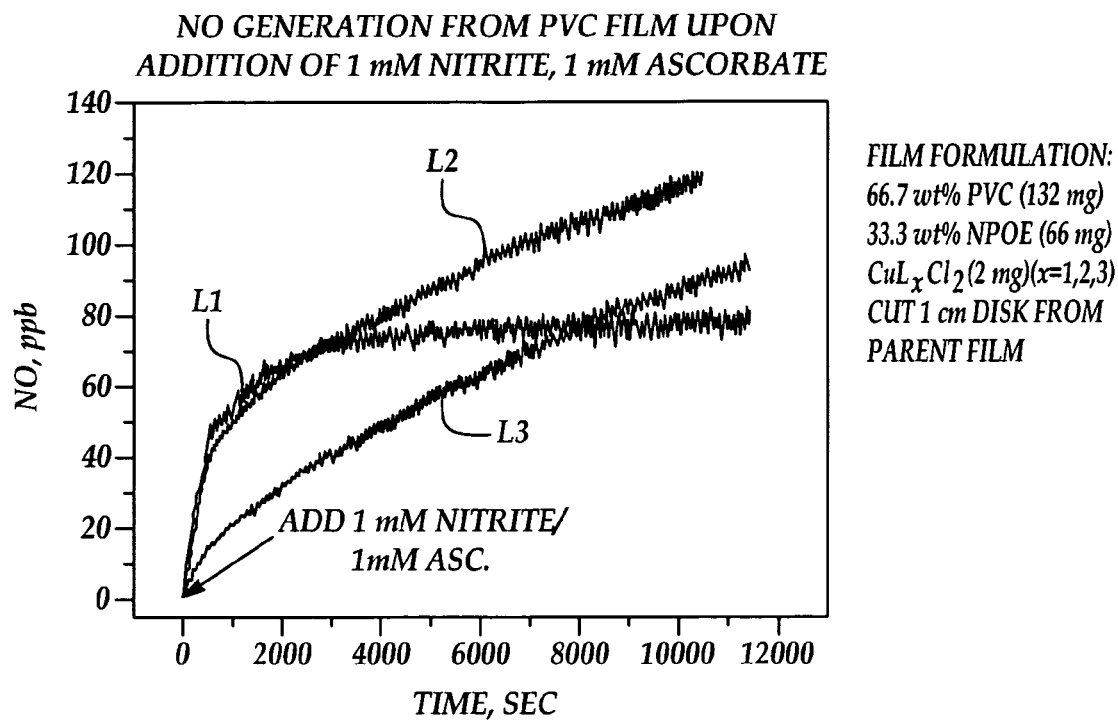
FIG. 5 is a graphical representation of the surface generation of NO from a Cu(II) ligand complex-containing polymer film in a bulk solution containing nitrite and ascorbate.

FIG. 5 is a graphical representation of the surface generation of NO from a Cu(II) ligand complex-containing polymer film in a bulk solution containing nitrite and ascorbate. The data is plotted as NO concentration in parts per billion (ppb) as a function of time in seconds.

Figure 6:
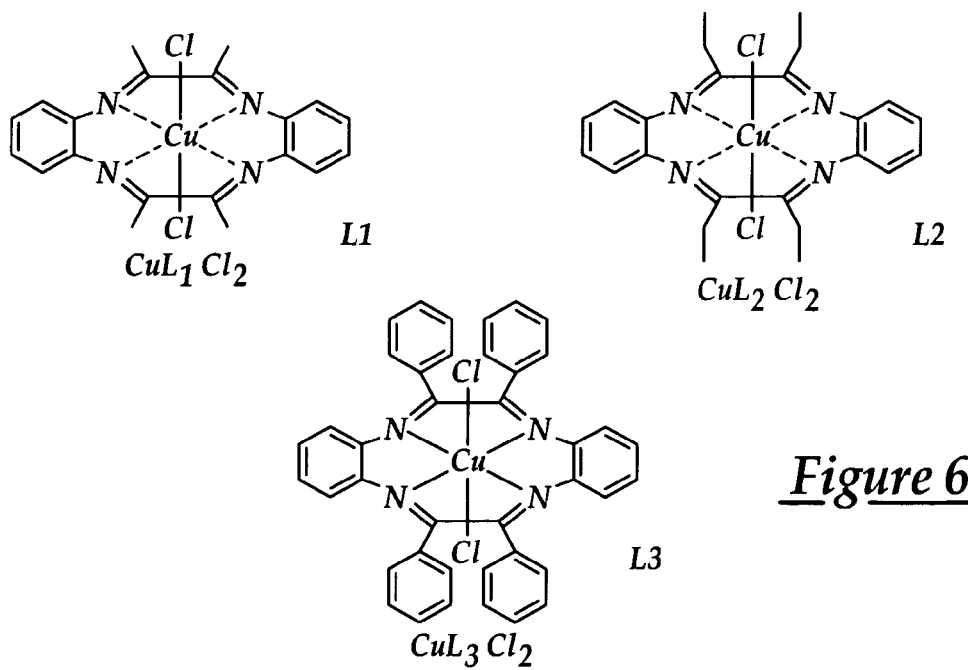
FIG. 6 shows three examples of illustrative metal ligand complexes.

Three films having the following formulation were prepared in accordance with the method set forth above: 66.7 wt % PVC polymer (132 mg); 33.3 wt % plasticizer, illustratively nitrophenyloctyl ether (NPOE; 66 mg), and Cu(II) ligand complex, $CuL_xCl_2$ (2 mg), $L_x$ being one or more of ligands L1-L3 as shown on FIG. 6. The illustrative metal ligand complexes, specifically Cu(II) ligand complexes, shown in FIG. 6 are dibenzo[e,k]-2,3,8,9-tetramethyl-1,4,7,10-tetraaza-cyclododeca-1,3,7,9-tetraene, labeled L1; dibenzo[e,k]-2,3,8,9,-tetraethyl-1,4,7,10-tetraaza-cyclododeca-1,3,7,9-tetraene, labeled L2; and dibenzo[e,k]-2,3,8,9-tetraphenyl-1,4,7,10-tetraaza-cyclodeca-1,3,7,9-tetraene, labeled L3.

Although these complexes are shown as chloride salts, it is to be understood that other counterions are appropriate. Other metal ions were evaluated for activity, i.e., ability to mediate the reduction of nitrite to NO by ascorbate, including Co(II), Ni(II), Zn(II) Mn(II), Al(II), and Fe(III). Of these ions, Fe(III) yielded a detectable level of NO, but this was far less than that observed with Cu(II) under identical conditions. Other metals, such as V(III), Cr(III), and Ti(III) have also been suggested as being capable of reducing nitrite to NO. However, unlike Cu(II) or Fe(III), these metals are not present in appreciable levels in vivo, either within physiological fluids or within specialized cellular vesicles. Therefore, Cu(II) is presently the preferred metal ion for the practice of the invention.

Referring back to FIG. 5, the traces represent ligands L1-L3, respectively. In this particular experiment, the bulk solution was deoxygenated phosphate buffered saline (PBS) having a pH of 7.4. At time t=0, 1 mM nitrite and 1 nM ascorbate were added to the PBS solution and NO generation was measured with a chemiluminescense detector. The results demonstrate that films in accordance with the present invention are capable of NO generation at the interface when the nitrites and ascorbates are in the bulk solution, such as would occur when the films were placed in contact with blood in an in vivo situation.

Figure 7:
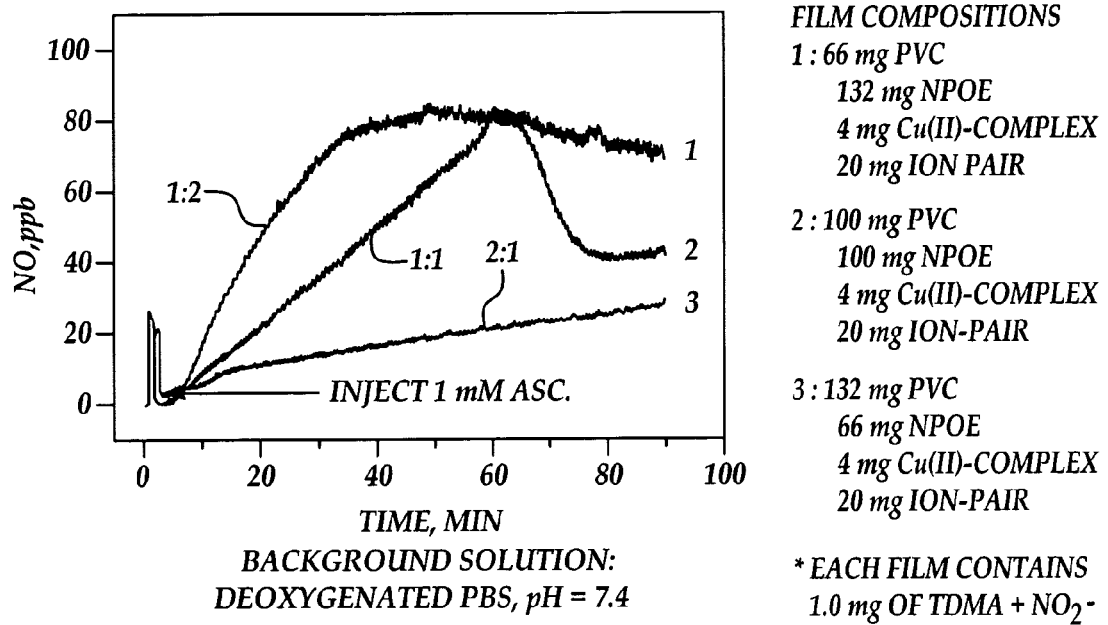
FIG. 7 is a graphical representation of NO generation from a nitrite ion pair/Cu(II) complex, specifically the complex designated L2 in FIG. 6.

FIG. 7 is a graphical representation of NO generation from a nitrite ion pair/Cu(II) complex, specifically the complex designated L2 in FIG. 6, doped into a polymer film. The data is plotted as NO concentration in parts per billion (ppb) as a function of time in minutes following the introduction of 1 mM ascorbate into a deoxygenated PBS solution having pH 7.4.

The polymeric film compositions used in this experiment are as follows:

Film 1:
66 mg PVC; 132 mg NPOE; 4 mg Cu(II) complex; and 20 mg ion pair or TDMA$^+$NO$_2^-$ Film 2:
100 mg PVC; 100 mg NPOE; 4 mg Cu(II) complex; and 20 mg ion pair Film 3:
132 mg PVC; 66 mg NPOE; 4 mg Cu(II) complex; and 20 mg ion pair These results show generation of NO by the polymer film that is particularly good for the highly plasticized embodiments.

The major advantage of this technology over the previous methods for generating NO locally at the surface of polymers or other materials is the potential simplicity of simply dip-coating the material with a biocatalytic or biomimetic catalytic layer. The catalytic layer may have a single catalyst or a mixture of reductase activities. It may be a biological protein (enzyme) or a metal ion-ligand complex that mimics the enzyme function. Even in those embodiments where added TDMA$^+$ NO$_2^-$/NO$_3^-$ or some other nitrite/nitrate salt, or a nitrosothiol, such as nitroso cysteine, is required or desired, within the material, the stability of such species is likely to far exceed the stability of diazeniumdiolates and other NO donors used to date.

In a clinical situation, it should be noted that, even if the amount of reducing equivalent species in the blood were to vary from test subject to test subject, it is possible to add reducing equivalents of an alternate electron donor to the blood, illustratively in the form of ascorbic acid, by administering low doses of Vitamin C to the patient. This may aid in ensuring the presence of adequate levels of reducing equivalents.

Although the invention has been described in terms of specific embodiments and applications, persons skilled in the art can, in light of this teaching, generate additional embodiments without exceeding the scope or departing from the spirit of the invention described herein. Accordingly, it is to be understood that the drawing and description in this disclosure are proffered to facilitate comprehension of the invention, and should not be construed to limit the scope thereof.

What is claimed is:

1. An NO releasing material, comprising:
   a polymer;
   a neutral carrier ligand having a planar square geometry; and
   a metal ion bound to the neutral carrier ligand;
   wherein said material generates nitric oxide when in contact with a nitrate, a nitrite or a nitrosothiol.

2. The NO releasing material of claim 1 wherein said neutral carrier ligand is at least one of: a $N_x$-donor macrocyclic ligand or a $S_x$-donor macrocyclic ligand, wherein x is independently selected from the group consisting of 2, 4, 5, 6 or 8.

3. The NO releasing material of claim 2 wherein said ligand is a $N_x$-donor macrocyclic ligand selected from: cyclen, cyclam or derivatives thereof, or a crown ether.

4. The NO releasing material of claim 1 wherein said metal ion is selected from Fe(III) or Cu(II).

5. The NO releasing material of claim 1 wherein the polymer is selected from polyurethane, polydimethylsiloxane, ethylene vinyl acetate, nylon, polyacrylic, polymethyl methacrylate, polyamide, polycarbonate, polyester, polyethylene, polypropylene, polystyrene, polytetrafluoroethylene, cellulose acetate, poly(vinyl chloride), and silicone rubber.

6. A biocompatible material comprising a metal coated with the NO releasing material of claim 1.

7. A medical device comprising the NO releasing material of claim 1.

8. An NO releasing material, comprising:
   a polymer;
   a neutral carrier ligand having a planar square geometry; and
   a metal ion bound to the neutral carrier ligand;
   wherein said material generates nitric oxide when in contact with a nitrate, a nitrite or a nitrosothiol;
   and wherein said ligand is selected from dibenzo[e,k]-2,3,8,9-tetraphenyl-1,4,7,10-tetraaza-cyclododeca-1,3,7,9-tetraene; dibenzo[e,k]-2,3,8,9-tetramethyl-1,4,7,10-tetraaza-cyclododeca-1,3,7,9-tetraene; dibenzo[e,k]-2,3,8,9-tetraethyl-1,4,7,10-tetraaza-cyclododeca-1,3,7,9-tetraene, and/or salts thereof.

* * * * *